United States Patent [19]

Reilly

[11] Patent Number: 5,156,958
[45] Date of Patent: Oct. 20, 1992

[54] GENE ENCODING A 30 KILODALTON OUTER MEMBRANE PROTEIN OF BORDETELLA PERTUSSIS AND METHOD OF RECOMBINANT PRODUCTION OF SAID PROTEIN

[75] Inventor: Patricia A. Reilly, Glen Rock, N.J.

[73] Assignee: American Cyanamid Company, Wayne, N.J.

[21] Appl. No.: 586,347

[22] Filed: Sep. 21, 1990

[51] Int. Cl.$^5$ .................. C12P 21/02; C12N 1/21; C12N 15/70; C12N 15/31
[52] U.S. Cl. .................. 435/69.1; 435/252.33; 435/320.1; 536/27
[58] Field of Search .................. 435/69.1, 71.2, 252.3, 435/320, 849; 536/27

[56] References Cited

PUBLICATIONS

DeBoer et al. Methods in Enzymology 185:103–110, 1990.
West et al. Due Acid Res. Nov., 1985: 9323–9335.
Cunningham et al. 1973, Biochemistry 12:4811.
Naniatis et al. 1982, Cloning Manual Cold Spring Harbor Laboratory.
Armstrong et al, 1986 Intect. Immun. 15:865.
Nonji et al. 1985, Intect Immun. 54:308.

Primary Examiner—Richard A. Schwartz
Assistant Examiner—John L. LeGuyader
Attorney, Agent, or Firm—Karen A. Lowney

[57] ABSTRACT

The present invention relates to a nucleotide and amino acid sequence of a 30 kilodalton outer membrane protein of *Bordetella pertussis*. The invention also relates to host cells and vectors comprising the nucleotide sequence, as well as a vaccine composition comprising the substantially pure protein.

12 Claims, 6 Drawing Sheets

```
CAGGATTTGCTCCCATATCCCATTCATGCACTTGCCTGGATGCCAAGCACCCTCTCCA    60

GACAACGCCAAGTAAACATTCAAAGGTCAAAGGACATACATGAAACGCATCGCCATGCT   120
                                    MetLysArgIleAlaMetLeu
                                                    -15

GGCTGCTGCTGCGTCATTGCCGTGCCCGCTTTCGCCCAGAACGTGGCGACCGTGAACGG   180
AlaAlaAlaCysValIleAlaAlaValProAlaPheAlaGlnAsnValAlaThrValAsnGly
        -10                    -5                       1

CAAGCCCATTACTCAGAAGAGCCTGGATGAGTTCGTCAAGCTGGTCGTCAGCCAGGGCGC   240
LysProIleThrGlnLysSerLeuAspGluPheValLysLeuValValSerGlnGlyAla
              10                    15                    20                    25

TACCGATTCGCCCCAGCTGCGTGAGCAGATCAAGCAGGAAATGATCAACCGCCAGTGTT   300
ThrAspSerProGlnLeuArgGluGlnIleLysGlnGluMetIleAsnArgGlnValPhe
        30                    35                    40                    45

CGTGCAGGCGGCCGAGAAGGACGGCGTCGCCAAGCAGGCCGACGTGCAGACTGAGATCGA   360
ValGlnAlaAlaGluLysAspGlyValAlaLysGlnAlaAspValGlnThrGluIleGlu
        50                    55                    60                    65

GCTGGCCGCCGACGGAGTCCTGGTGCGCCCTGATGGCCGACTACCTGCAAAAACACACCC   420
LeuAlaArgHisGlyValLeuValArgAlaLeuMetAlaAspTyrLeuGlnLysHisPro
        70                    75                    80                    85
```

FIG. 1a

```
CGTCACCGACGCCCAGGTCAAGGCCCAATACGAAAAGATCAAGAAAGAACAGGCCGGCAA  480
ValThrAspAlaGlnValLysAlaGluTyrGluLysIleLysLysGluGlnAlaGlyLys
       90                95               100              105

GATGGAATACAAGGTCCGTCACATCCTGGTCGAGGACGAAAAGACGGCCAACGACCTGCT  540
MetGluTyrLysValArgHisIleLeuValGluAspGluLysThrAlaAsnAspLeuLeu
      110               115               120              125

GGCCCAGGTCAAGAGCAACAAGAACAAGTTCGACGATCTGGCCAAGAAGAACTCCAAGGA  600
AlaGlnValLysSerAsnLysAsnLysPheAspAspLeuAlaLysLysAsnSerLysAsp
      130               135               140              145

CCCCGGCAGCCCGAGCGCGGCGGACCTGGGTTGGCGCTGCACCAACTACGTCCAGCC  660
ProGlySerProSerAlaAlaAlaThrTrpValGlyArgCysThrAsnTyrValGlnPro
      150               155               160              165

GTTTGCCGAGGCCGTGACCAAGCTGAAGAAGGCCAACTGGTCGACAAGCCGGTGCAGAC  720
PheAlaGluAlaValThrLysLeuLysLysGlyLeuValAspLysProValGlnThr
      170               175               180              185

CCAGTTCGGCTGGCACGTGATCCAGGTCGACGATACCCGTCCGGTCGAATTCCCGCCAT  780
GlnPheGlyTrpHisValIleGlnValAspThrArgProValGluPheProAlaMet
      190               195               200              205
```

FIG. 1b

```
GGACCAGGTGGCGCCCGCCAACTGGAAGAAATGCTGCGCCAGCAAACCCTGGCCAACTACCA  840
AspGlnValArgProGlnLeuGluGluMetLeuArgGlnThrLeuAlaAsnTyrGln
         210                 220                 225          230

GAAGCAATGGCGGCGAACAGGCCAAGATCCAGTAAGGCCAAGCCATCGCCATCAACAAAA    900
LysGlnLeuArgGluGlnAlaLysIleGln
         235                 240

TTGCCCGCTTCGCGGGAATTTGTTTTCGGCTGCCCGGGGCGCCGCTTCGCCTAA          960
```

FIG.1c

|       | 1 | 2 | 3 | 4 |
|-------|---|---|---|---|
| (KDa) |   |   |   |   |
| 97.4 —|   |   |   |   |
| 66.2 —|   |   |   |   |
| 45 —  |   |   |   |   |
| 31 —  |   |   |   |   |
| 21.5 —|   |   |   |   |
| 14.4 —|   |   |   |   |

FIG. 2A

|       | 1 | 2 | 3 | 4 |
|-------|---|---|---|---|
| (KDa) |   |   |   |   |
| 97.4 —|   |   |   |   |
| 66.2 —|   |   |   |   |
| 45 —  |   |   |   |   |
| 31 —  |   |   |   |   |
| 21.5 —|   |   |   |   |
| 14.4 —|   |   |   |   |

FIG. 2B

|      | | | | | | | | | | | | | |
|---|---|---|---|---|---|---|---|---|---|---|---|---|---|
| AvaI | | | | | | | | | | | | | 4 C'yCGr_G |
| BglI | | | | | | | | | | | | | 8 GCCn_nnn'nGGC |
| EcoRI | | | | | | | | | | | | | 2 G'_AATT_C |
| KpnI | | | | | | | | | | | | | 1 G_GTAC'C |
| PstI | | | | | | | | | | | | | 1 C_TGCA'G |
| PvuII | | | | | | | | | | | | | 1 CAG'CTG |
| SalI | | | | | | | | | | | | | 3 GTCGA_C |
| SphI | | | | | | | | | | | | | 2 G_CATG'C |

ENZYMES THAT DO NOT CUT:

BglII

FIG.3

5,156,958

GENE ENCODING A 30 KILODALTON OUTER MEMBRANE PROTEIN OF BORDETELLA PERTUSSIS AND METHOD OF RECOMBINANT PRODUCTION OF SAID PROTEIN

FIELD OF THE INVENTION

The present invention relates to a DNA and amino acid sequence of a 30 Kilodalton outer membrane protein of *Bordetella pertussis*. The protein in question is antigenic and therefore, the recombinantly produced protein may be used in vaccine compositions to protect against *B. pertussis* infection. It is also useful as an adjuvant in vaccine compositions against other microorganisms such as *Haemophilus influenza*. The isolated gene sequence also permits construction of recombinant vectors and host cells useful in producing the protein.

BACKGROUND OF THE INVENTION

The bacterium *Bordetella pertussis* is the causative agent of whooping cough or pertussis. It is currently routine to immunize infants and small children against *B. pertussis* with a vaccine comprising whole thermally or chemically inactivated *B. pertussis* cells. Although such vaccines are widely used and are very effective in inducing protection, such whole cell preparations necessarily contain components which are not necessary to achieve protection and which may in fact cause undesirable side effects in association with immunization. It is, therefore, preferable to identify those cellular components which are essential to immunity and utilize only those required to achieve the desired effect.

*B. pertussis* exhibits many proteins which are potential candidates for such a component vaccine formulation. Among these are lymphocytosis promoting factor (Morse and Morse, J. Exp. Med. 143: 1483–1502, 1976), filamentous hemagluttinin (Cowell et al, in Robbins et al, eds., Bacterial Vaccines, Thieme Stratton, Inc., N.Y., pp. 371–379); and agglutinogens (Eldering et al, J. Bacteriol. 74: 133–136, 1957). Also of recent interest are a number of virulence—associated cell envelope proteins. (Armstrong and Parker, Infect. Immun. 54: 308–314, 1986); Parker and Armstrong, Rev. Infect. Dis. 10 (Suppl. 2): S327–S330, 1988). One or more of these outer membrane components has previously been used as an adjuvant in a vaccine formulation containing *Haemophilus influenza* e as the active immunogen (U.S. Pat. No. 4, 474,758). Outer membrane proteins also are present in an acellular pertussis vaccine produced by Takeda by copurification of several pertussis proteins.

Of particular interest to the present invention is an outer membrane protein of 30 kilodaltons. A "virulence associated doublet", referred to as Omp 30/32 has previously been described by Parton and Wardlaw. (J. Med Microbiol. 8:47-57, 1975) A 30 KD fraction of the *B. pertussis* outer membrane proteins was found to be particularly useful in enhancing immune response to *H. influenzae* capsular polysaccharide (Monji et al., Infect. Immun. 51: 865–871, 1986). Although the protein per se has been isolated, isolation depends upon chemical separation from the bacterial outer membrane and other outer membrane proteins. There has not previously been a means for producing the protein in large quantities by any other method. The present invention now makes available an alternative means for production of the 30 KD protein in high yield without resort directly to the bacterial source.

SUMMARY OF THE INVENTION

The present invention provides a novel isolated gene and nucleic acid sequence encoding a 30 kilodalton outer membrane protein of *Bordetella pertussis*. Also provided is a complete deduced amino acid sequence of the protein.

The availability of the gene sequence of the 30 KD protein permits the expression of the protein in a variety of host cells. Thus, the invention also encompasses a method for producing a purified 30 KD *B. pertussis* outer membrane protein which comprises transforming a host cell with the 30 KD gene, and culturing the host cell under conditions which permit expression of the gene in the host cell. Recovery of the protein can be made directly from the host cell, or from the culture supernatant depending upon the mode of expression in the host. Transformation of host cells may be achieved either directly by naked nucleic acid or by expression vectors engineered to carry the sequence of the 30 KD protein. The invention thus also provides host cells transformed with the claimed nucleic acid sequence, as well as expression vectors comprising the sequence.

The 30 KD protein is useful as the primary immunogen in a vaccine composition to provide protection against *B. pertussis* infection. The transformed host cells provide a convenient means for production of substantially pure (i.e., obtained free of normal cellular contaminants, and at least preferably about 90% pure) 30 KD protein. Protein so produced forms the basis of a subunit vaccine comprising an effective amount of a substantially pure 30 KD protein, or immunogenic portion thereof, in combination with a pharmaceutically acceptable carrier. Also encompassed by the invention is a method for immunizing an individual against *B. pertussis* infection which comprises administering to an individual in need of such protection an effective amount of the aforementioned vaccine composition.

BRIEF DESCRIPTION OF THE FIGURES

FIG. 1 (ports a, b and c) shows the nucleotide and predicted amino acid sequence.

FIG. 2 shows expression of recombinant 30K protein in *E. coli* strain JM109 (DE3). Lane 1. standards, Lane 2. JM 109 (DE3)+pCLL1101 after induction, cell lysate, Lane 3. passed fraction from Affigel-blue column, Lane 4. passed fraction from DE53 column A Coomassie Blue stained SDS-gel. B. Western blot probed with anti-sera to native 30K.

FIG. 3 shows a restriction map of *B. pertussis* DNA fragment containing the gene for 30K outer membrane protein. The open reading frame for 30K gene is between base 770 and ,1544.

FIG. 4 (parts a and b) shows a comparison of 30K and r30K protein by peptide mapping. 5 ug of native (A) or recombinant 30K (B) was loaded in each lane of 15% SDS-polyacrylamide gel with 0 ug (1), 2.5 ug (2), or 5 ug (3) endoproteinase Glu-C and digested in the gel. The gel was transferred to Nitroplus 2000 and developed with antisera to native 30K protein and protein A-Horseradish peroxidase.

DETAILED DESCRIPTION OF THE INVENTION

The DNA sequence encoding the 30 KD protein is originally cloned by screening of a λ gtll library containing genomic DNA of *Bordetella pertussis.* Recombinant phage that express the 30 KD protein are identified by plaque lift (Mierendorf et al, Meth. Enzymol. 152: 458-469, 1987) using rabbit antisera against the 30 KD protein. Positive recombinant clones are identified and phage DNA isolated. Pertussis DNA is removed and subcloned into a plasmid vector for restriction mapping, and into an M13 bacteriophage (Messing et al, Nucl. Acids Res. 9: 307, 1981) for DNA sequence analysis.

The gene containing the 30 KD protein is isolated on an approximately 3.5 kb fragment of pertussis DNA. Approximately 2.5 kb is sequenced using the Sanger dideoxy termination method (PNAS USA 74: 5463-5467, 1977) from both single stranded M13 and double stranded plasmid subclones, generated by exonuclease III deletion subcloning methods. The DNA sequence of the 30 KD protein is presented in FIG. 1.

The recombinant protein consists of a sequence of 242 amino acids, also shown in FIG. 1. The protein is expressed in *E. coli* using the T7 RNA polymerase and promoter system (Studier et al., Meth. Enzymol. 185: 60-69, 1990). The open reading frame encoding the 30 KD protein is cloned into a pGEM 7Zf+plasmid behind a T7 RNA polymerase promoter. The resulting plasmid is designated pCLL 1101. The plasmid is transformed into *E. coli* strain JM109 (DE3) containing the T7 RNA polymerase gene under the control of the lac UV5 promoter. Expression of the T7 RNA polymerase is induced by the addition of isopropyl-B-D-thiogalactopyranoside (IPTG). The presence of the 30 KD protein is confirmed by Western blotting of whole cell lysates, shown in FIG. 2B.

The expressed protein is purified from lysates of IPTG—induced bacterial cultures. The protein obtained after a two—step column chromatography purification is approximately 90% pure. The recombinant purified protein from *E. coli* is compared to the 30 KD native purified protein from *B. pertussis*. The native and recombinant proteins have the same apparent molecular weight as determined by SDS-PAGE, the same isoelectric point (about 9) as determined by isoelectric focusing, both cross-react with anti-30 KD antisera, and both have the same peptide mapping pattern when digested with endoproteinase Glu-C.

The following examples illustrate the cloning and expression of the 30 KD protein gene in a T7 RNA polymerase expression system. However, although this T7 expression system has proven quite efficient, it is to be understood that this is not the only means by which 30 KD protein can be produced recombinantly. Production of the protein can be achieved by incorporation of the gene into any suitable expression vector and subsequent transformation of an appropriate host cell with the vector; alternately the transformation of the host cells can be achieved directly by naked DNA without the use of a vector. Production of the protein by either eukaryotic cells or prokaryotic cells is contemplated by the present invention. Examples of suitable eukaryotic cells include mammalian cells, plant cells, yeast cells and insect cells. Similarly, suitable prokaryotic hosts, in addition to *E. coli*, include *Bacillus subtilis*.

Other suitable expression vectors may also be employed and are selected based upon the choice of host cell. For example, numerous vectors suitable for use in transforming bacterial calls are well known. For example, plasmids and bacteriophages, such as λ phage, are the most commonly used vectors for bacterial hosts, and for *E. coli* in particular. In both mammalian and insect cells, virus vectors are frequently used to obtain expression of exogenous DNA. In particular, mammalian cells are commonly transformed with SV40 or polyoma virus; and insect cells in culture may be transformed with baculovirus expression vectors. Yeast vector systems include yeast centromere plasmids, yeast episomal plasmids and yeast integrating plasmids.

It will also be understood that the practice of the invention is not limited to the use of the exact sequence of the gene as defined in FIG. 1. Modifications to the sequence, such as deletions, insertions, or substitutions in the sequence which produce silent changes in the resulting protein molecule are also contemplated. For example, alteration in the gene sequence which reflect the degeneracy of the genetic code, or which result in the production of a chemically equivalent amino acid at a given site, are contemplated; thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, are also expected to produce a biologically equivalent product. Nucleotide changes which result in alteration of the N-terminal and C-terminal portions of the protein molecule would also not be expected to alter the activity of the protein. Therefore, where the phrase "30 KD protein DNA sequence" or "30 KD protein gene" is used in either the specification or the claims, it will be understood to encompass all such modifications and variations which result in the production of a biologically equivalent 30 KD protein. In particular, the invention contemplates those nucleic acid sequences which are sufficiently duplicative of the sequence of FIG. 1 so as to permit hybridization therewith under standard high stringency southern hybridization conditions, such as those described in Maniatis et al., (Molecular Cloning. A Laboratory Manual, 2nd ed. Cold Spring Harbor Laboratory, 1989), or encode proteins which react with antisera to native 30 KD protein.

In addition to a full length gene and protein, the invention encompasses fragments of each. In particular, the invention encompasses nucleic acid fragments encoding peptides, and the peptides per se, which retain the antigenicity of the parent molecule. Preferably the fragments in question encode peptides containing epitopes which elicit production of protective antibodies. In addition to preparation by recombinant methods, such smaller peptides can also be prepared synthetically by known peptide synthesis techniques.

The gene product in purified form, or a synthetic immunogenic peptide is useful in the preparation of a vaccine composition for prevention of pertussis. Either the whole protein, or any active portion thereof, can be employed as an immunogenic agent in such a composition. The protein prepared by recombinant methods can be isolated from host cells by standard protein isolation techniques. The purified protein is then combined with any of the commonly used acceptable carriers such as water, physiological saline, ethanol, polyols, such as glycerol or propylene glycol, or vegetable oils, as well as any of the vaccine adjuvants known as the art. The proteins may also be incorporated into liposomes for use in a vaccine preparation. As used herein "pharmaceutically acceptable carriers" is to encompass any and all solvents, dispersion media, coatings and antifungal agents, isotonic and absorption delaying agents and the like. Except insofar as any conventional medium is incompatible with the active ingredient, its use in the therapeutic composition is contemplated.

In addition to its use as the sole active agent in a vaccine composition, the 30 KD protein, or active portions thereof, may also be combined with other active agents. For example, a pertussis vaccine may comprise the 30 KD protein with one or more purified and isolated outer membrane proteins, or other known immunogenic proteins from *Bordetella pertussis*. Moreover, the 30 KD protein may be combined as an active component with immunogenic agents against other infectious diseases, such as influenza, hepatitis, or herpes. Also, the 30 KD protein may be used in vaccine compositions, in adjuvant effective amounts, to improve the immune response to other immunogenic agents, such as those noted above.

The microorganisms and other biological materials referred to herein are retained in the collections of American Cyanamid Company, Lederle Laboratories, Pearl River, New York, and *E. coli* strain JM109 (DE 3) containing plasmid pCLL1101, has been deposited with the American Type Culture Collection, 12301 Parklawn Drive, Rockville, Md., on Sep. 18, 1990, as ATCC 68402.

The invention is further illustrated by the following non-limiting examples.

EXAMPLES

1. Cloning of 30 KD gene from λqtll library

Genomic DNA is isolated from *B. pertussis* strain 130. EcoRI linkers are added to mechanically sheared DNA and then cloned into the EcoRI site of λgtll. The library contains approximately $1.6 \times 10^6$ independent clones. The library is diluted $1:10^5$, for each 150 mm plate, 0.1 ml is mixed with 0.6 ml of *E. coli* strain Y1090 and incubated at room temperature for 20 min. The cells are plated in 7.5 ml LB top agar on LB plates and incubated for 3 hr at 42° C. Nitrocellulose filters are soaked in 10 mM IPTG and air dried. These are laid on the plates which are incubated at 37° C. for 3 hr. The filters are blocked with 10 mM Tris-HCl, pH 8.0, 150 mM NaCl, 0.05% Tween 20 (TBST) plus 1% bovine serum albumin (BSA) overnight. The filters are washed in TBST and anti-30K sera is added. Following a 60 min incubation the filters are washed again with TBST, then incubated with Protein A—Horseradish Peroxidase conjugate for 60 min. The filters are washed in TBS (10 mM Tris-HCl, ph 8.0, 150 mM NaCl) and then incubated in the presence of the Horse-radish peroxidase substrate (4-chloro-1-napthol and hydrogen peroxide in TBS). Positive plaques are picked and eluted into SM 6.1 M NaCl, 10 mM MgSO4, 50 mM Tris HCl, pH7.5, 0.01% gelatin) buffer. Positive phage are plaque purified by repeating the screening procedure.

2 Sequencing of the 30 KD gene

Approximately 3.6 kb fragment of pertussis DNA is isolated from positive λ clones. Two EcoRI fragments (1.4 and 2.2 kb) are subcloned into M13mp18 for sequencing by the dideoxytermination method. Exonuclease III deletion subclones are generated to sequence overlapping subclones (Henikoff, S. (1984) Gene 28: 357). The EcoRI site is located in the middle of the open reading frame. To confirm the sequence across this junction, plasmid clones containing the entire open reading frame are sequenced using Sequenase (US Biochemicals). Since pertussis DNA has a high G+C content, regions of compression are sequenced in both directions. A restriction map of the 30 KD protein gene is provided in FIG. 3. Comparison of this map with that shown in Shareck and Cameron (J. Bacteriol. 159: 780–782, 1984; FIG. 2) shows that the gene of the present invention does not encode the 30 Kd protein disclosed by these authors.

3. Expression and purification of recombinant 30 KD Protein

Pertussis DNA is isolated from positive phage and subcloned into pGEM7zf+ for expression. A 3 kb KpnI—SacI fragment of pertussis DNA is cloned into pGEM7zf+ after the T7 RNA polymerase promoter (designated pCLL 1101) and transformed into the *E. coli* host strain JM109 (DE3) which contains the T7 RNA polymerase gene under the control of the lacUV5 promoter. Cultures of JM109 (DE3) containing pCLL 1101 are grown in LB plus ampicillin (50 μg/ml) at 37° C. to an OD of 1 at 550 nm. IPTG is added to a final concentration of 0.5 mM and cultures incubated for an additional 3 hr. Cells are harvested by centrifugation 5,000×g for 10 minutes and washed with water. The cell pellet is resuspended in 10 ml lysis buffer (50 mM Tris-HCl, pH8.0, 1 mM EDTA, 100 mM NaCl), 0.3ml lysozyme (10 mg/ml in lysis buffer) is added and the mixture incubated at room temperature for 30 min. As the viscosity increases 0.07ml DNase (1 mg/ml in lysis buffer) is added. The mixture is centrifuged at 15,000×g for 30 min at 4° C. The supernatant is centrifuged at 200,000×g for 30 min. The supernatant fraction is passed over an Affigel Blue column in 50 mM Tris-HCl, pH 7.4. The flow through fraction is collected and passed over a DE53 column in 50 mM Tris-HCl, pH 8.0. These two chromatography steps result in a preparation of recombinant 30 KD protein which is approximately 90% pure.

4. Characterization of the recombinant 30 KD protein

Purified 30 KD protein from *B. pertussis* is compared to the recombinant protein purified from *E. coli* by several methods. The proteins when fractionated by SDS-PAGE on a 12.5% acrylamide gel migrate to identical apparent molecular weight. Western blot analysis shows the proteins both cross-react with antisera against the native 30 KD protein. In addition, the native and recombinant protein focus at a pI of approximately 9 in isoelectric focusing gels. The predicted pI of the mature protein based on the amino acid sequence deduced from the DNA sequence is 9.8.

In order to confirm the identity of the recombinant protein, peptide mapping is done as described by D. W. Cleveland (Meth. Enzymol., vol 96, p. 222–229, 1983). Approximately 10 μg protein is loaded on a 15% polyacrylamide gel in the presence of increasing amounts of endoproteinase Glu-C (0, 2.5, 5 μg) in digestion buffer consisting of 50 mM Tris-HCl, pH 6.8, 10% glycerol and 0.1% SDS. The samples are electrophoresed into the stacking gel and current turned off for 1 hr to allow digestion. The current is turned on and resulting peptides separated. One gel is stained with Coomassie Brilliant Blue and a second electrotransferred to nitrocellulose membrane for Western blot analysis. Both the native and recombinant protein have the same peptide digestion pattern. One difference that is observed between the native and recombinant proteins is the native protein has a blocked amino-terminus. This is not the case with the recombinant 30K protein, where the first 50 amino acids have been determined by protein sequencing.

What is claim is:

1. An isolated nucleic acid sequence encoding a 30KD outer membrane protein of *Bordetella pertussis* wherein the sequence hybridizes with a nucleic acid sequence encoding the amino acid sequence of FIG. 1.

2. The sequence of claim 1 which encodes a full-length protein having an isoelectric point of about 9.

3. The sequence of claim 1 which comprises the sequence depicted in FIG. 1.

4. An expression vector comprising the gene of claim 1.

5. The vector of claim 4 which is a plasmid.

6. The vector of claim 5 which is pCLL1101.

7. A host cell transformed with the gene of claim 1.

8. The cell of claim 7 which is deposited with the American Type Culture Collection as ATCC 68402.

9. A method of producing a substantially pure 30 kd outer membrane protein of *Bordetella pertussis* which comprises transforming a host cell with the nucleic acid sequence of claim 1, and culturing the host cell under conditions which permit expression of the nuclei acid sequence by the host cell.

10. The method of claim 9 in which the bacterial cell is *E. coli*.

11. The method of claim 9 in which transformation is achieved by an expression vector.

12. The method of claim 11 in which the expression vector is pCLL 1101.

* * * * *